United States Patent
Hansen et al.

(10) Patent No.: US 7,972,558 B2
(45) Date of Patent: Jul. 5, 2011

(54) METHOD AND AN APPARATUS FOR STERILIZING PACKAGING MATERIAL

(75) Inventors: Lasse Hansen, Brøndby Strand (DK); Anders Dossing Norskov, København (DK); Per Jeppensen, Brønshøj (DK); Signe Agnete Christensen, Humlebæk (DK)

(73) Assignee: Novo Nordisk A/S, Bagsvaerd (DK)

( * ) Notice: Subject to any disclaimer, the term of this patent is extended or adjusted under 35 U.S.C. 154(b) by 421 days.

(21) Appl. No.: 12/280,689

(22) PCT Filed: Feb. 28, 2007

(86) PCT No.: PCT/EP2007/051900
§ 371 (c)(1),
(2), (4) Date: Dec. 1, 2008

(87) PCT Pub. No.: WO2007/099120
PCT Pub. Date: Sep. 7, 2007

(65) Prior Publication Data
US 2009/0148340 A1    Jun. 11, 2009

Related U.S. Application Data

(60) Provisional application No. 60/780,036, filed on Mar. 7, 2006.

(30) Foreign Application Priority Data

Feb. 28, 2006    (EP) ..................... 06004073

(51) Int. Cl.
| | | |
|---|---|---|
| A61L 2/00 | (2006.01) |
| B01J 19/00 | (2006.01) |
| B65B 31/00 | (2006.01) |
| B65B 29/00 | (2006.01) |
| B65B 55/02 | (2006.01) |
| A45C 11/04 | (2006.01) |
| A61B 17/06 | (2006.01) |
| G01N 21/01 | (2006.01) |
| G01N 23/00 | (2006.01) |
| A21D 10/02 | (2006.01) |
| A23L 3/00 | (2006.01) |
| B65D 85/84 | (2006.01) |

(52) U.S. Cl. ................. 422/22; 422/23; 422/24; 422/41; 53/401; 53/425; 53/111 RC; 206/5.1; 206/438; 206/484; 206/524.4; 206/524.2; 206/828; 250/427; 250/732 R; 250/455.11; 250/492.1; 250/492.3; 426/118; 426/234; 426/321; 426/395

(58) Field of Classification Search ............ 422/22–24, 422/41; 53/401, 425, 111 RC; 206/5.1, 438, 206/484, 524.4, 524.2, 828; 250/427, 732 R, 250/455.11, 492.1, 492.3; 426/118, 234, 426/321, 395

See application file for complete search history.

(56) References Cited

U.S. PATENT DOCUMENTS

| 3,780,308 A | 12/1973 | Nablo |
| 4,035,981 A | 7/1977 | Braun et al. |
| 5,904,960 A | 5/1999 | Becraft et al. |
| 6,355,216 B1 | 3/2002 | Kristiansson et al. |
| 2001/0035500 A1 | 11/2001 | Schianchi et al. |

FOREIGN PATENT DOCUMENTS

| JP | 11084100 | 3/1999 |
| WO | WO 02/072157 | 9/2002 |
| WO | WO 2004/110869 | 12/2004 |
| WO | WO 2005/000580 | 1/2005 |
| WO | WO 2005/061222 | 7/2005 |

*Primary Examiner* — Jill Warden
*Assistant Examiner* — Monzer R Chorbaji
(74) *Attorney, Agent, or Firm* — Wesley A. Nicolas; Marc A. Began (57) ABSTRACT

A method and an apparatus for sterilizing packaging material for use in packaging for protein containing products, such as food products or medical drugs. The packaging material is sterilized by irradiating it using a beam of ionizing radiation, such as an electron beam or a beam of gamma rays. Afterwards, the packaging material is processed in such a manner that protein reactive substances or compounds formed in the packaging material during the irradiation step are at least partly removed or rendered inreactive with respect to proteins. The processing step may advantageously be performed by heating the packaging material. Preferably, the processing step involves accelerating diffusion from the packaging material of protein reactive substances or compounds. Since the protein reactive substances or compounds are removed or rendered inreactive with respect to proteins, degradation of the product which is later stored in the packaging material is considerably reduced. The packaging material needs to be stored under sterile conditions for a shorter period of time. Thereby the space needed for sterile storage, as well of the risk of contamination, is considerably reduced.

24 Claims, 6 Drawing Sheets

Fig. 9 ized substances mentioned above are very reactive with respect to proteins. Furthermore, once they have been formed in the polymer material, there is a risk that they will migrate into the product being contained in the packaging, and thereby react with proteins present in the product, leading to the undesired effects described above.
METHOD AND AN APPARATUS FOR STERILIZING PACKAGING MATERIAL

CROSS-REFERENCE TO RELATED APPLICATIONS

This application is a 35 U.S.C. §371 national stage application of International Patent Application PCT/EP2007/051900 (published as WO 2007/099120 A1), filed Feb. 28, 2007, which claimed priority of European Patent Application 06004073.0, filed Feb. 28, 2006; this application further claims priority under 35 U.S.C. §119 of U.S. Provisional Application 60/780,036, filed Mar. 7, 2006.

FIELD OF THE INVENTION

The present invention relates to a method and an apparatus for sterilizing packaging material, in particular packaging material for use in packaging in which it is intended to store a substance, such as protein containing products or a drug. More particularly, the present invention relates to a method and an apparatus in which sterilizing is performed using ionizing radiation, e.g. a beam of ionizing radiation.

BACKGROUND OF THE INVENTION

When manufacturing packaging and packaging material for products which need to be packaged under more or less sterile conditions, the packaging must be sterilized before the products are positioned or wrapped in the packaging. Examples of such products are food products and pharmaceuticals, in particular liquid pharmaceuticals.

It is known to sterilize packaging or packaging material for such products by directing a beam of ionizing radiation, e.g. an electron beam or a beam of gamma rays towards the packaging material. This is, e.g. described in WO 02/072157, U.S. Pat. No. 3,780,308 and U.S. Pat. No. 4,035,981. However, such a beam of ionizing radiation may cause chemical reactions in the packaging material. This may result in the formation of compounds or substances which are reactive with respect to proteins. Thus, if the product is positioned in the packaging immediately after the sterilization, these compounds or substances may react with proteins which are present in the product, thereby leading to undesired alterations of the product. In case the product is a food product, such alterations may cause the taste of the product to be altered in an undesired manner. In case the product is a pharmaceutical the reactive compounds or substances may cause alterations in an active component of the pharmaceutical, and this may lead to alterations in the therapeutic effect of the pharmaceutical, possibly in such a manner that the therapeutic effect of the pharmaceutical may be unknown and even varying from one package to another. This is very undesirable.

The situation described above is in particular a problem when the packaging material is or comprises a polymer material. In this case irradiation of the material using ionizing radiation may cause carbon-carbon bonds and/or carbon-hydrogen bonds of the polymer material to break, and/or it may cause pieces of polymer (e.g. comprising 3-6 carbon atoms) to become detached from the original polymer chain. The result may be the formation of free radicals or smaller molecules which may potentially migrate from the irradiated packaging material into the product or substance being stored in the packaging material, and/or the formation of compounds comprising hydrocarbon and oxygen, e.g. aldehydes, ketones, alcohols or carboxylic acid. All of the compounds or substances mentioned above are very reactive with respect to proteins. Furthermore, once they have been formed in the polymer material, there is a risk that they will migrate into the product being contained in the packaging, and thereby react with proteins present in the product, leading to the undesired effects described above.

One way to address this problem is to allow a time period to lapse from the irradiation of the packaging material until the product is positioned or wrapped in the packaging. The lapsed time period should be sufficient to ensure that the undesired compounds or substances react spontaneously, e.g. with ambient air molecules, or evaporates from the packaging material. Such a process is, e.g., described in WO 02/072157, disclosing a method of producing sterile prefilled syringe bodies. The syringe bodies are sterilized using a beam of ionizing radiation and transferred to a sterile environment, and the syringe bodies are maintained in a sterilized condition as they are transferred to the sterile environment. A fluid substance is provided and introduced into the syringe body while the syringe body is within the sterile environment. The syringe bodies are filled within 5 days of the irradiation, but it is preferred that they are filled after approximately 15 minutes.

It is a disadvantage that it is necessary to allow a time period to lapse between irradiation of the packaging material and positioning the product in the packaging, because it adds to the total processing time. In particular, it adds to the time the packaging needs to be maintained in a sterile environment. This causes requirements to the sterile environment in terms of available storage space. Furthermore, the sterile environment needs to be positioned in immediate vicinity of the irradiation station, or the transport from the irradiation station to the sterile environment must be carried out very carefully and under strict sterile conditions. Otherwise there is a risk that the sterilized packaging material will be contaminated before the product can be positioned in the packaging and the packaging is sealed. This introduces the risk that the product is in fact not positioned in a sterile packaging, and the product may therefore also be contaminated, possibly introducing a health risk to a user.

WO 2004/110869 discloses a method and a device for ventilating a device for electron beam irradiation of a web. Irradiation of the web is performed while the web is moved through an irradiation chamber. While the web is irradiated a flow of gaseous fluid is created in the irradiation chamber in a direction opposite to the moving direction of the web. Thereby ozone created in the air surrounding the web is removed. The method and the device disclosed in WO 2004/110869 do not solve the problems described above, since the flow of gaseous fluid has no, or only a limited, effect on protein reactive substances or compounds which may be formed in the packaging material during irradiation. Furthermore, the flow of gaseous fluid is moved along the web during the irradiation, and protein reactive substances or compound formed at the end of the irradiation process will therefore not be affected by the flow of gaseous fluid.

JP 11084100 discloses a device for sterilizing objects. The objects are moved past an irradiation station, and then into an aseptic room container in order to prevent the objects from being contaminated again after irradiation. The surface of the aseptic room container may be sterilized by means of heating. In order to sterilize the surface of the aseptic room container by means of heating, a relatively high temperature, such as above 300° C., must be provided in the aseptic room container, and the device disclosed in JP 11084100 will therefore not be suitable for sterilizing packaging material made from a polymer material.

Packaging and packaging materials which are suitable for storing liquid solutions or suspensions, such as medicaments are disclosed in WO 2005/000580 and WO 2005/061222, which are hereby incorporated by reference.

SUMMARY OF THE INVENTION

It is, thus, an object of the invention to provide a method for sterilizing packaging material or packaging for protein containing products, in which the necessary time lapse between an irradiation step and positioning the product in the packaging is reduced as compared to prior art methods, while ensuring that degradation of the product is prevented to the greatest possible extent.

It is a further object of the invention to provide a method for sterilizing packaging material or packaging for protein containing products, in which the requirements to storage facilities for the sterilized packaging can be reduced as compared to prior art methods, in particular in terms of available storage space and sterility.

It is an even further object of the invention to provide a method for sterilizing packaging material or packaging for protein containing products, the method being suitable for packaging material made from a polymer material.

The present invention relates to a method for sterilizing packaging material for use in packaging for a substance, the method comprising the steps of:
 irradiating the packaging material using ionizing radiation,
 processing the irradiated packaging material in such a manner that substances or compounds formed in the packaging material during the irradiation step, and which are potentially damaging for the substance to be stored in the packaging material, are at least partly removed or rendered inreactive with respect to the substance.

The substance may, e.g., be a protein containing product or a drug. Representative drugs include pharmaceuticals, such as peptides, proteins and hormones, biologically derived or active agents, hormonal and gene based agents, nutritional formulas and other substances in both (dispensed) or liquid form.

According to a first aspect of the invention the above and other objects are fulfilled by providing a method for sterilizing packaging material for use in packaging for protein containing products, the method comprising the steps of:
 irradiating the packaging material using ionizing radiation,
 subsequently accelerating diffusion from the packaging material of protein reactive substances or compounds formed in the packaging material during the irradiation step.

According to a second aspect of the invention the above and other objects are fulfilled by providing an apparatus for sterilizing packaging material for use in packaging for protein containing products, the apparatus comprising:
 an irradiation station comprising means for emitting ionizing radiation towards the packaging material,
 a processing station comprising means for processing the irradiated packaging material in such a manner that diffusion of protein reactive substances or compounds formed in the packaging material during irradiation is accelerated, and
 means for conveying the packaging material at least between the irradiation station and the processing station.

In the present context the term 'packaging material' should be interpreted to mean a material which it is suitable to use when packaging is manufactured. Such packaging could, e.g., be a container, a box, a vial, a canister, a cartridge, a bag, a lid for a container or a box, etc. In the present context packaging which is at least partly formed by the sterilized packaging material will be suitable for storing protein containing products. This will be explained in further details below.

In the present context the term 'protein containing product' should be interpreted to mean a product in which proteins form an important part. Such products may, e.g., be food products or medical drugs. The medical drugs may be solid, e.g. tablets, liquid, e.g. an injectable drug, or gaseous, e.g. an inhalable drug. As mentioned above such products may undergo undesirable changes if they get into contact with protein reactive substances or compounds, and it is therefore important that packaging for such products, or at least a part of the packaging which is likely to get into direct contact with the product, is at least substantially free from protein reactive substances or compounds.

Irradiating the packaging material using ionizing radiation will sterilize the packaging material as described above. Thus, the actual sterilization of the packaging material takes place during the irradiation step. The irradiation may advantageously take place by directing a beam of ionizing radiation towards the packaging material.

In the present context the term 'protein reactive substances or compounds' should be interpreted broadly to mean substances or compounds which are likely to react chemically with proteins. Examples of protein reactive substances or compounds are free radicals, carbon chains, e.g. of 3-6 carbon atoms, and volatiles, such as aldehydes. Aldehydes are particularly problematic because they are extremely reactive with respect to proteins. Thus, even small concentrations of aldehydes may cause substantial degradation in the product being stored in the packaging, and it is therefore very desirable to remove aldehydes from the packaging material or render them inreactive with respect to proteins.

During the irradiation step protein reactive substances or compounds may be formed in the packaging material because the ionizing radiation reacts with the packaging material, thereby causing, e.g., carbon-carbon bonds or carbon-hydrogen bonds to break, thereby forming the reactive substances or compounds. The protein reactive substances or compounds may be formed in a surface region and/or in a bulk region of the packaging material.

The substances or compounds which are present in a surface region are, naturally, very likely to get into contact with a product which is at a later time stored in packaging formed by the packaging material, and it is therefore very important to remove these substances or compounds, or to render them inreactive with respect to proteins. Once the protein reactive substances or compounds get into contact with the product they may diffuse into the product, react with protein in the product and thereby damage the product as described above.

The substances or compounds which are formed in a bulk region may either be relatively 'free to move', or they may be 'fixed' in the bulk. In case they are 'free to move', there is a risk that they will diffuse to the surface area where they may get into contact with the product and damage it as described above. It is therefore important that this kind of substances or compounds are removed or rendered inreactive with respect to proteins. In case the substances or compounds are 'fixed' in the bulk region, there is a very small risk that they will get into contact with product stored in the packaging because the product is unlikely to enter the bulk region of the packaging material and the compounds or substances are unlikely to leave the bulk region. In most cases it will therefore be of less importance to remove this kind of substances or compounds or render them inreactive with respect to proteins.

The means for conveying the packaging material may be or comprise one or more conveyor belts, rollers, chutes, pushers, and/or any other suitable kind of conveying means.

Subsequently to the irradiation step, the step of accelerating diffusion from the packaging material of protein reactive substances or compounds formed in the packaging material during the irradiation step is performed. Thereby protein reactive substances or compounds which have formed in the packaging material during the irradiation step are at least partly removed or rendered inreactive with respect to proteins. Furthermore, by accelerating the diffusion, this is obtained within a much shorter time than would be the case if one merely waited until the substances or compounds have diffused from the packaging material by themselves. Preferably, at least the substances or compounds which are at risk of getting into contact with a product which is stored in the packaging at a later time should be removed. As an alternative, removing substances or compounds may, e.g., be done by evaporating the substances or compounds from the packaging material. As another alternative, rendering the substances or compounds inreactive with respect to proteins may, e.g., be done by causing the substances or compounds to react with other compounds, thereby chemically altering the substances or compounds in such a way that they are no longer protein reactive.

When the packaging material is processed as described above it is ensured that the protein reactive substances or compounds which are formed in the packaging material during the irradiation step are prevented from reacting with protein contained in a product which is at a later time stored in the packaging. Furthermore, this is ensured in a controlled and deliberate manner, thereby avoiding waiting for the substances or compounds to disappear or react spontaneously. Thus, long time storage in a sterile environment is no longer required. This is very advantageous.

Furthermore, since the step of accelerating diffusion is performed subsequently to the irradiation step, it can be ensured that diffusion of all the protein reactive substances or compounds formed in the packaging material during the irradiation step is accelerated, including the substances or compounds which are formed at the end of the irradiation step. This is also an advantage.

The irradiating step may be performed using an electron beam, i.e. the ionizing radiation may be in the form of a beam of electrons directed towards the packaging material. In this case an electron beam of approximately 180 keV and 3.6 mA may be used, and the packaging material may be pulled through the electron beam at a velocity of approximately 7-10 m per minute. The applied radiation dose may be varied by varying the velocity at which the packaging material is pulled through the electron beam. The applied dose may preferably be within the interval 15 kGy to 100 kGy.

Alternatively, the ionizing radiation may be in the form of electromagnetic radiation, such as in the form of a beam of electromagnetic radiation, such as a beam of gamma rays or a beam of ultraviolet (UV) light.

Thus, the means for emitting a beam of ionizing radiation may comprise an electron beam emitter, a gamma ray generator or a UV generator.

The step of accelerating diffusion may be performed in such a manner that diffusion of protein reactive substances or compounds formed in a surface region of the packaging material is accelerated. As described above, there is a high risk that protein reactive substances or compounds formed in a surface region of the packaging material get into contact with a protein containing product stored in the packaging, and it is therefore very important to remove these substances or compounds or render them inreactive with respect to proteins. In case no protein reactive substances or compounds are formed in the bulk region of the packaging material, or in case substances or compounds formed in the bulk region are 'fixed', it may even be sufficient to accelerate diffusion of the ones formed in the surface region to ensure that a protein containing product can be safely stored in the packaging. However, the method may further comprise the step of accelerating diffusion of protein reactive substances or compounds formed in the bulk region of the packaging material.

The step of accelerating diffusion may comprise heating the irradiated packaging material, e.g. to a temperature which does not exceed 200° C., such as to a temperature which does not exceed 175° C., such as to a temperature which does not exceed 125° C., such as to a temperature within the temperature interval 40° C. to 95° C., such as to a temperature within the temperature interval 50° C. to 70° C. Thus, the processing means may comprise means for heating the packaging material. The temperature should in any case not exceed a temperature beyond which the packaging material may suffer damage. Thus, for some polymer materials, e.g. polyethylene, the temperature should preferably not exceed 90° C., because polyethylene typically starts melting at this temperature. For other kinds of polymers, e.g. polypropylene, the temperature may be allowed to become somewhat higher, e.g. up to approximately 165° C., or even higher. Some polymers do not start melting before they reach a temperature of approximately 400° C. Depending on the kind and properties of the protein reactive substances or compounds, heating the packaging material may have various effects resulting in the substances or compounds being removed or rendered inreactive with respect to proteins, besides accelerating diffusion of the protein reactive substances or compounds. For instance, the heating may result in chemical changes to the substances or compound, e.g. by oxidizing the substances or compounds, or it may result in evaporation of the substances or compounds from the packaging material. Chemical reactions and evaporation may also take place spontaneously. However, by heating the packaging material these processes take place faster and in a more controlled manner, and the desired result is therefore reached faster and more reliably.

It has been discovered by the inventors of the present invention that heating the packaging material after irradiation actually prevents potentially damaging substances or compounds from entering the product which is subsequently stored in the packaging material. Thus, water samples which had been stored in irradiated packaging material were analysed for the presence of such compounds or substances. Some of the samples had been stored in packaging material which had been heated after the irradiation, and some had been stored in packaging material which had not been heated. It turned out that in the water samples which had been stored in packaging material which had not been heated, potentially damaging compounds or substances were present. These compounds and substances were not present in the water samples which had been stored in packaging material which had been heated.

The heating may take place during a specific time, e.g. within the range 5 s to 300 s.

The heating step may be performed using infrared radiation provided by an IR source. In this case the heating step may advantageously be performed by applying 2 times 900 W for 3-5 s. Alternatively, the heating may be performed by means of a heat gun which is directed towards the packaging material.

Alternatively, the heating step may be performed using an oven. In this case the packaging material may advantageously be positioned in an oven for a certain time period, e.g. by conveying the packaging material through the oven, or by manually or automatically positioning the packaging material in the oven, leave it there for a certain time period, and removing it from the oven again, manually or automatically.

As another alternative, the heating step may be performed by applying a flow of heated air to the packaging material.

Alternatively or additionally, the step of accelerating diffusion may comprise subjecting the packaging material to a vacuum, e.g. by positioning the packaging material under vacuum, i.e. subjecting the packaging material to a relatively low pressure. In this case the low pressure will cause the protein reactive substances or compounds to diffuse from the packaging material to the ambient, and as a consequence they will no longer be present in the packaging material when the packaging material is removed from the vacuum. Thus, the vacuum enhances and speeds up a natural evaporation process, and it is therefore not necessary to wait for the substances or compounds to evaporate spontaneously.

In one embodiment the step of accelerating diffusion may be performed substantially immediately after the irradiation step, such as within 5 min. after the irradiation step, preferably within 2 min. after the irradiation step, more preferably within 30 s after the irradiation step, most preferably within a few seconds after the irradiation step. In this case the time from sterilization of the packaging material takes place until the packaging is ready to receive a product to be stored is minimised. Thereby the risk of contamination of the packaging material before the product is received in the packaging is also minimised. Furthermore, the need for storage of the packaging material under sterile conditions is also minimised. This is very advantageous, in particular when the product to be stored is a pharmaceutical, because in this case it is very important to avoid contamination.

The method may further comprise the step of forming a packaging, at least part of said packaging being made from the packaging material. All of the packaging may be made from the packaging material, or only a part of the packaging, e.g. a lid or a seal, may be made from the packaging material. The step of forming a packaging may advantageously be performed either prior to the irradiation step or after the processing step. In case it is performed prior to the irradiation step it is the packaging which undergoes irradiation and acceleration of diffusion, and the packaging will therefore be ready to receive a product when the step of accelerating diffusion has been completed. This is advantageous because it is thereby possible to reduce to time elapsing from sterilization of the packaging to the product is received in the packaging and the packaging sealed, and the risk of contamination is thereby minimised.

The packaging material may be a foil, and the step of forming a packaging may comprise welding two foil layers together, thereby forming a reservoir. The two foil layers may be from separate foils. Alternatively, one foil may be folded and welded, thereby forming the reservoir.

Thus, a product may be stored in the packaging. The method, in this case, preferably further comprises the step of sealing the packaging, thereby avoiding contamination of the product.

In case the step of forming a packaging is performed after the step of accelerating diffusion, the packaging is formed by the sterilized and processed packaging material. This is in particular advantageous in case only part of the packaging is made from the packaging material, e.g. a lid, a covering foil, a cap or a sealing part. In this case the sterilized and processed packaging material may be applied to the remaining part of the packaging with the product arranged therein, e.g. during a sealing process.

The method steps may advantageously form an inline process. According to this embodiment the process steps are performed at least substantially immediately subsequently to each other. Thereby the time elapsing from the irradiation step until the packaging with the product is ready to leave the processing plant is minimised, thereby providing an efficient procedure with a low risk of contamination of the products and reduced need for storage under sterile conditions. This reduces the manufacturing costs.

Preferably, the packaging material may be a polymer material, e.g. a film material. The polymer or film material used may be a polymer of polyethylene (herein designated PE), polypropylene (herein designated PP), polyethylene terephalate (herein designated PET) and/or polychlorotrifluoroethylene (herein designated PCTFE) and these polymers may be used alone or together.

The film material should preferably, after sterilization, fulfill some or all the following physical requirements: 1) the material must be transparent, 2) the material must provide a good barrier against water; 3) the material must provide a good barrier against gasses (for example, oxygen and carbon dioxide); 4) the material must provide a good barrier against preservatives (for example, phenol and meta-cresol); 5) the material must provide a good barrier against odors (for example preservatives); 6) the material must be resistant against environmental stress cracking (for example, oils, perfumes); 7) the material must be resistant against flex-crack; 8) the material must have good sealing properties (for example, by welding); 9) the material must not delaminate after sterilization, during processing or storage; and 10) the material must not relax significantly during storage and use.

Alternatively other materials may be used, such as glass.

According to one embodiment, the steps of the method may be performed in a sterile environment. Thereby the risk of contamination is even further reduced. However, since the complete procedure may be performed relatively fast as described above, the total size of the sterile environment may be reduced as described above.

According to a third aspect of the invention the above and other objects are fulfilled by providing a method of processing a material containing protein reactive substances or compounds, the method comprising the step of accelerating diffusion from the material of protein reactive substances or compounds.

Thus, the third aspect of the invention relates to a method for accelerating diffusion of protein reactive substances or compounds, regardless of the origin of these substances or compounds.

According to a fourth aspect of the present invention the above and other objects are fulfilled by providing a method for sterilizing polymer packaging material for use in packaging for protein containing products, the method comprising the steps of:

irradiating the polymer packaging material using ionizing radiation, subsequently processing the polymer packaging material in such a manner that protein reactive substances or compounds formed in the polymer packaging material during the irradiation step are at least partly removed or rendered inreactive with respect to proteins, positioning a protein containing product in packaging formed by the polymer packaging material, and sealing the packaging having the protein containing product positioned therein, wherein the processing step is performed in such a manner that an impurity level in the protein containing product after storage in the packaging for 10 weeks at 5° C. is within 1.5% of a corresponding impurity level in a comparable protein containing product positioned in a packaging made from a sterilized glass material under similar storage conditions.

It should be noted that a person skilled in the art would readily recognise that any feature described in combination with the first aspect may also be combined with the second, the third and the fourth aspects, any feature described in combination with the second aspect may also be combined with the first, the third and the fourth aspects, any feature described in combination with the third aspect may also be combined with the first, the second and the fourth aspects, and any feature described in combination with the fourth aspect may also be combined with the first, the second and the third aspects.

The processing step is performed in such a manner that an impurity level in the protein containing product after storage in the packaging for 10 weeks at 5° C. is within 1.5% of a corresponding impurity level in a comparable protein containing product positioned in a packaging made from a sterilized glass material under similar storage conditions. When a glass material is sterilized using ionizing radiation, protein reactive substances or compounds are normally not formed, and it is therefore safe to position a protein containing product in packaging made from a glass material immediately after irradiation. Accordingly, storage in a glass material can be used as a reference with respect to the impurity level in a packaging material having a protein containing product positioned therein. However, glass materials have some disadvantages as compared to polymer materials. For instance, they are not flexible and they are fragile.

Preferably, the processing step is performed in such a manner that an impurity level in the protein containing product after storage in the packaging for 2 years at 5° C. is within 1.5% of a corresponding impurity level in a comparable protein containing product positioned in a packaging made from a sterilized glass material under similar storage conditions, preferably within 0.5-1%.

Thus, according to the fourth aspect of the invention, a packaging material is provided in which a protein containing product will be as stable, or almost as stable, as a corresponding product stored in a glass material, and at the same time the advantages of polymer material, such as flexibility, robustness, etc., are obtained. This is very advantageous.

The processing step may be performed by accelerating diffusion from the packaging material of protein reactive substances or compounds formed in the packaging material during the irradiation step. This has been described in further detail above with reference to the first and second aspects of the invention, and the remarks set forth in that connection are equally applicable here.

Alternatively or additionally, the processing step may comprise heating the packaging material, e.g. to a temperature which does not exceed 200° C., such as to a temperature within the temperature interval 40° C. to 95° C. The heating step may be performed by applying a flow of heated air to the packaging material, by using infrared radiation, or by using an oven. This has also been described above.

Alternatively or additionally, the processing step may comprise subjecting the packaging material to a vacuum as described above.

BRIEF DESCRIPTION OF THE DRAWINGS

The invention will now be described in further details with reference to the accompanying drawings in which.

DETAILED DESCRIPTION OF THE DRAWINGS

Figure 1:
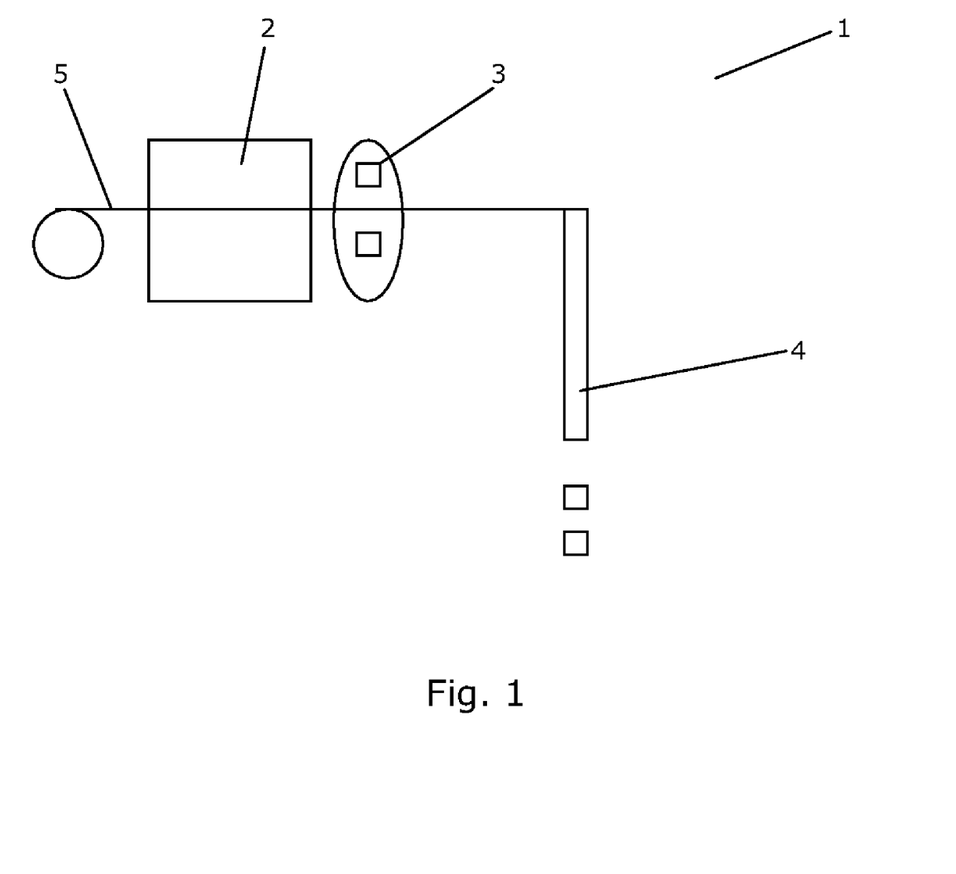
FIG. 1 is a diagrammatic view of a sterilization system according to an embodiment of the invention.

FIG. 1 is a diagrammatic view of a sterilization system 1 according to an embodiment of the invention. The sterilization system 1 comprises an irradiation station 2, a heating station 3 and a filling station 4.

A polymer film 5 is conveyed past the irradiation station 2. Thereby the film 5 is irradiated with an electron beam (e.g. a 180 keV, 35 kGy electron beam). The film 5 is then conveyed to the heating station 3 where it is subjected to heating. The heating may be performed in any suitable way, such as using an IR source, a heat gun or an oven, and the time and temperature of the heating may be selected appropriately. The heating of the film 5 has the effect that any undesired protein reactive substances or compounds which were formed during the irradiation step are removed or rendered inreactive with respect to proteins, preferably by accelerating diffusion of the substances or compound from the film.

Immediately after the heating, the film 5 is formed into reservoirs which are conveyed to the filling station 4. At the filling station 4 medication, such as insulin, is filled into the reservoirs, and the reservoirs are sealed in order to conserve the medication.

Since protein reactive substances or compounds which may have been formed in the polymer film 5 during irradiation are removed or rendered inreactive with respect to proteins during the heating, degradation of the medication which is filled into the reservoirs at the filling station 4 is considerably reduced. Thereby sterilized packaging is provided in which degradation of medication stored in the packaging due to reaction between the medication and undesired substances or compounds in the packaging material is reduced or even avoided.

Figure 2:
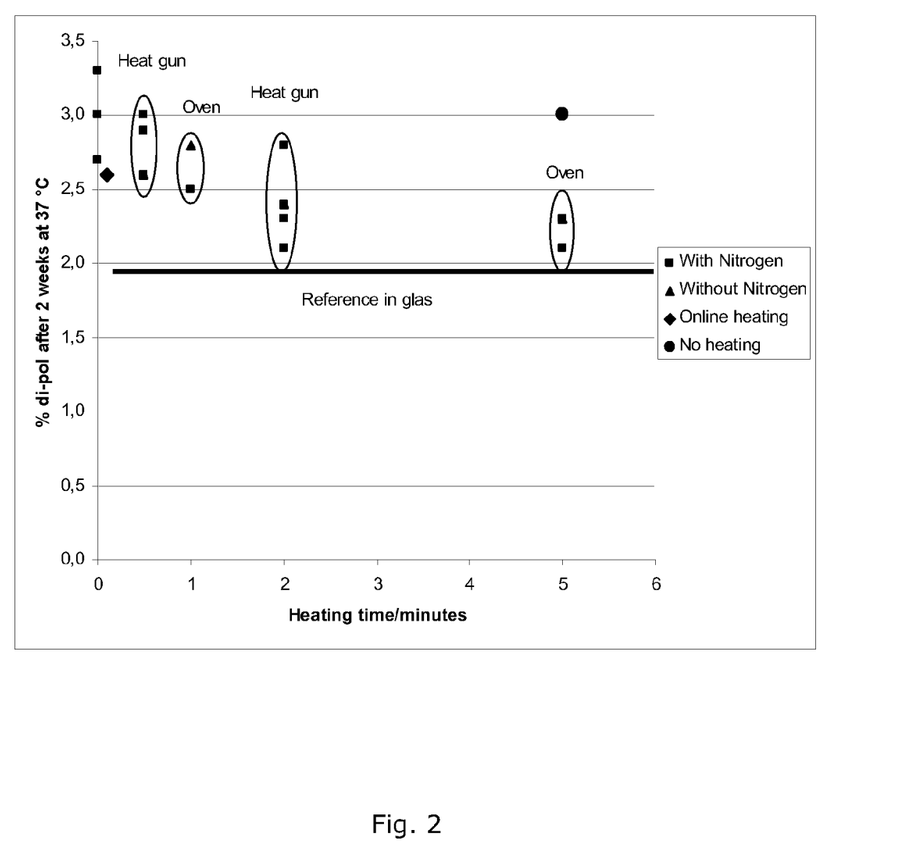
FIG. 2 is a graph illustrating the percentage of di- and polymers present in insulin stored for two weeks at 37° C. in packaging which has been sterilized in accordance with various embodiments of the invention.

FIG. 2 is a graph illustrating the percentage of di- and polymers present in insulin stored for two weeks at 37° C. in packaging which has been sterilized in accordance with various embodiments of the invention. The packaging may advantageously have passed through the sterilization system 1 shown in FIG. 1. The heating time as well as the manner of heating the packaging material was varied, as illustrated by the legend of FIG. 2. Thus, the heating was performed using a heat gun and an oven, respectively. The irradiation step was performed in a nitrogen atmosphere and in atmospheric air, respectively. Furthermore, two reference samples were prepared, one in an irradiated polymer packaging which had not been heated, and one in a conventional glass ampoule ('reference in glass'). Since glass is not expected to contain protein reactive substances or compounds, the latter reference sample may be regarded as representing an ideal situation where no protein reactive substances or compounds are present.

At the filling station 4 insulin was filled into the reservoirs. After sealing, the reservoirs were stored at 37° C. for two weeks. The contents of the reservoirs were then analysed and compared. In the situation illustrated in FIG. 2 the analysis was done by detecting the percentage of di- and polymers present in the insulin, i.e. the percentage of dimers and polymers of proteins from the insulin present in each reservoir. Such di- and polymers represent an important kind of degradation product, i.e. a large percentage of di- and polymers indicates a large degradation of the proteins of the insulin.

Comparing the results shown in FIG. 2, it is clear that the longer the heating time, the smaller the percentage of di- and polymers present in the insulin, indicating that the degree of degradation of the insulin is reduced when heating is applied to the packaging. This is particularly clear when the results from the heated samples are compared to the result of the sample in the packaging which was not heated. It also seems that using a nitrogen atmosphere improves the result as compared to performing the irradiation in atmospheric air.

It should be noted, that under normal circumstances the reservoirs with the insulin would be stored at approximately 5° C. rather than at 37° C. These storage conditions would reduce the degradation of the insulin as compared to the study illustrated in FIG. 2. Thus, the study illustrated in FIG. 2 may be regarded as performed under 'accelerated conditions'. However, the conclusion, i.e. that degradation is reduced if the irradiated packaging material is heated before the insulin is filled into the reservoirs, would be the same under normal storage conditions, even though the degradation would be somewhat slower.

Figure 3:
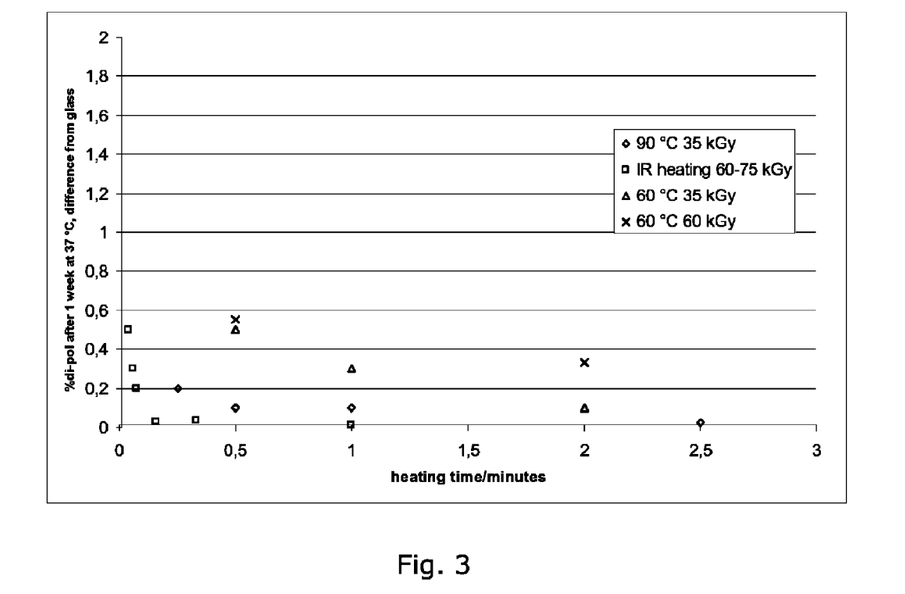
FIG. 3 is a graph illustrating the percentage of di- and polymers present in insulin stored for one week at 37° C. in packaging which has been sterilized in accordance with various embodiments of the invention, as compared to a reference sample stored in glass packaging.

FIG. 3 is a graph illustrating the percentage of di- and polymers present in insulin stored for one week at 37° C. in packaging which has been sterilized in accordance with various embodiments of the invention, as compared to a reference sample stored in glass packaging. The study illustrated in FIG. 3 is very similar to the study illustrated in FIG. 2. However, in this case the temperature applied during the heating was varied as illustrated by the legend, and the analysis was performed after one week storage at 37° C. Furthermore, before the results were plotted, the percentage of di- and polymers present in the reference sample which was stored in the glass packaging was subtracted from the analysis results.

It is clear from the graph in FIG. 3 that the reservoirs which were heated to 90° C. contain a smaller percentage of di- and polymers than the reservoirs which were heated to 60° C. Thus, a higher temperature is preferred. It must, however, be kept in mind that the temperature should not be so high that the packaging material is damaged, e.g. due to melting. Furthermore, as was also concluded in the study illustrated in FIG. 2, a longer heating time is preferred. Finally, it seems that the heating provided by IR (infrared) heating is very efficient. Thus, after a relatively short heating time, approximately 10 seconds, the percentage of di- and polymers present in the sample is almost as low as is the case for the reference sample in the glass ampoule. Accordingly, it seems that providing the heating by means of an IR source is very advantageous.

Figure 4:
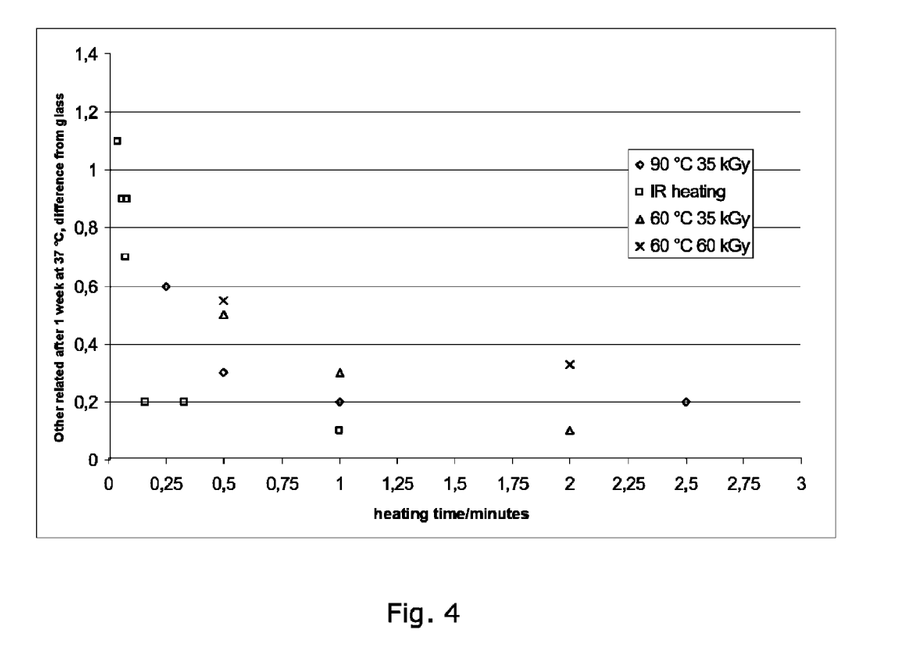
FIG. 4 is a graph illustrating the amount of other related degradation products present in insulin stored for one week at 37° C. in packaging which has been sterilized in accordance with various embodiments of the invention, as compared to a reference sample stored in glass packaging.

FIG. 4 is a graph illustrating the amount of other related degradation products present in insulin stored for one week at 37° C. in packaging which has been sterilized in accordance with various embodiments of the invention, as compared to a reference sample stored in glass packaging. Thus, the study illustrated in FIG. 4 is very similar to the study illustrated in FIG. 3. However, in this case the analysis is performed by detecting other related degradation products than di- and polymers. This parameter is also very important when regarding the total degradation of insulin. The conclusions are, however, the same as in the study illustrated in FIG. 3. Higher temperatures and longer heating times are preferred, and using an IR heating source is very efficient.

Example

Studies were made of insulin stored in irradiated polymer packaging in order to evaluate the effect of time and temperature of film prior to insulin filling, but after irradiation.

The effect of the above mentioned parameters were analysed by evaluating stability of insulin aspart U100.

Based on the results it can be concluded that time between irradiation and insulin/film contact has an impact on chemical stability of insulin aspart U100, that when heating of film between irradiation and filling is applied, the chemical stability of insulin aspart can be brought to the same level as if stored in glass vials, and that the heating times needed for a significant improvement in insulin stability is >30-60 seconds.

For the production of flexible reservoirs, the design of the production filling line is optimised for minimised chance of contamination of the film before insulin filling. Therefore the time between irradiation and insulin filling is planned to be held at a minimum. The line speed is planned to be 3 m/minute, and the time between irradiation and insulin filling will as a consequence be less than 2-3 minutes.

In several previous studies it has been observed that the film discolours when irradiated. The discoloration disappears after 20-30 minutes at room temperature. From this observation it is likely to conclude that chemical changes in the film do occur during and just after irradiation.

In earlier studies it has not been possible to keep the time between irradiation and filling production realistic. By the use of hand held welding equipment, a method for filling very shortly after irradiation was developed.

The above mentioned studies were initiated for the evaluation of insulin stability versus time between irradiation and filling. Furthermore the effect of heat treatment of the film prior to filling was evaluated.

The objective of the studies described in this example was to evaluate the effect of time and temperature of film prior to insulin filling, but after irradiation. The effect of the above mentioned parameters were analysed by evaluating stability of insulin aspart U100. Table 1 shows film test and test media.

TABLE 1

| Study | Film | Insulin aspart U100 batch |
|---|---|---|
| 1 | 1 | Batch 1 |
| 2 | 1 | Batch 2 |
| 3 | 2 | Batch 2 |
| 4 | 3 | Batch 3 |
| 5 | 3 | Batch 3 |

The films were comparable. Similarly, the insulin batches were comparable.

Films were irradiated and brought into contact with insulin aspart. The following parameters were controlled:
Dose of irradiation
Time between irradiation and filling
Temperature of film in the time span between irradiation and filling In study 1 the film was cut into pieces and immersed in insulin aspart U100. In study 2, 3, 4 and 5 the film was welded into reservoirs before filling. In all cases the time span between irradiation and insulin/film contact was controlled and noted.

The insulin aspart U100 was placed at 37° C., and sampling was performed in a period of 12 weeks. The results obtained will be described below.

The trends observed for related impurities are also valid for high molecular weight protein (HMWP) in the data obtained in studies described herein.

No difference in the level of B28isoAsp and desamido between aspart U100 stored in reservoirs and reference vials has been observed in stability data obtained from studies performed by the inventors of the present invention.

approximately 2-2.5% after 12 weeks at 37° C. For reservoirs allowed to rest for 60 minutes before filling the difference is approximately 1-1.5%.

In study 4 and 5 the temperature of the film between irradiation and filling was varied.

Table 2 shows data related to study 4. More particularly, the table shows levels of related impurities in reservoirs containing insulin aspart U100. The samples were stored at 37° C. The temperature was approximately 60° C. in all heating processes.

TABLE 2

| Test no. | Treatment | Dosis | Time = zero | 2 weeks | 6 weeks | 12 weeks |
|---|---|---|---|---|---|---|
| 1 | 30 sec. heat gun | 35 kGy (high dosis side) | 0.7 | 2.9 | 5.1 | 8.3 |
| 2 | 120 sec. heat gun | 35 kGy (high dosis side) | 0.7 | 2.1 | 4.4 | 7.8 |
| 3 | 60 sec heater | 35 kGy (high dosis side) | 0.8 | 2.5 | 5.2 | 8.4 |
| 4 | 5 min. heater | 35 kGy (high dosis side) | 0.8 | 2.3 | 4.4 | 8.0 |
| 5 | 30 sec. heat gun | 60 kGy (high dosis side) | 0.9 | 3.0 | 5.7 | 9.1 |
| 6 | 120 sec. heat gun | 60 kGy (high dosis side) | 0.9 | 2.8 | 4.7 | 8.2 |
| 6A | 120 sec. heat gun | 60 kGy (high dosis side) | 0.8 | 2.3 | 4.8 | 8.2 |
| 7 | 5 min. heater | 60 kGy (high dosis side) | 0.8 | 2.1 | 4.7 | 8.3 |
| 8 | 30 sec. heat gun | 60 kGy (low dosis side) | 0.9 | 2.6 | 4.9 | 8.5 |
| 9 | 120 sec. heat gun | 60 kGy (low dosis side) | 0.8 | 2.4 | 4.7 | 7.9 |
| 10 | 5 min. heater | 60 kGy (low dosis side) | 0.8 | 2.3 | 4.9 | 8.6 |
| 11 | | 35 kGy (high dosis side) | 1.1 | 3.0 | 5.6 | 9.5 |
| 12 | | 60 kGy (high dosis side) | 1.0 | 3.3 | 5.8 | 9.2 |
| 13 | | 60 kGy (low dosis side) | 0.9 | 2.7 | 5.5 | 8.8 |
| 14 | 60 min. from irradiation to filling | 60 kGy (high dosis side) | 0.8 | 2.5 | 5.4 | 9.0 |
| 15 | heat gun while the film comes ot of the machine | 60 kGy (low dosis side) | 0.8 | 2.6 | 5.1 | 8.5 |
| 16 | 5 min. from irradiation to filling | 60 kGy (high dosis side) | 1.0 | 3.0 | | 9.2 |
| 17 | | 0 kGy | 0.7 | 1.8 | 4.0 | 7.2 |
| 18 | 30 sec. heat gun | 35 kGy - N2 (high dosis side) | 0.9 | 2.6 | 5.0 | 8.9 |
| 19 | 120 sec. heat gun | 35 kGy - N2 (high dosis side) | 0.8 | 2.4 | 4.9 | 9.0 |
| 20 | 60 sec heater | 35 kGy - N2 (high dosis side) | 0.7 | 2.8 | 5.2 | 8.6 |
| 21 | 5 min. heater | 35 kGy - N2 (high dosis side) | 0.7 | 2.3 | 4.1 | 7.5 |
| Ref. | | | 0.7 | 1.9 | 3.9 | 7.1 |

This example only covers stability data from insulin stored at 37° C. In study 2 and 3 reservoirs were also placed at 5° C. storage.

In study 1 film pieces were immersed into insulin aspart after irradiation. Time between irradiation and immersion was varied.

Figure 5:
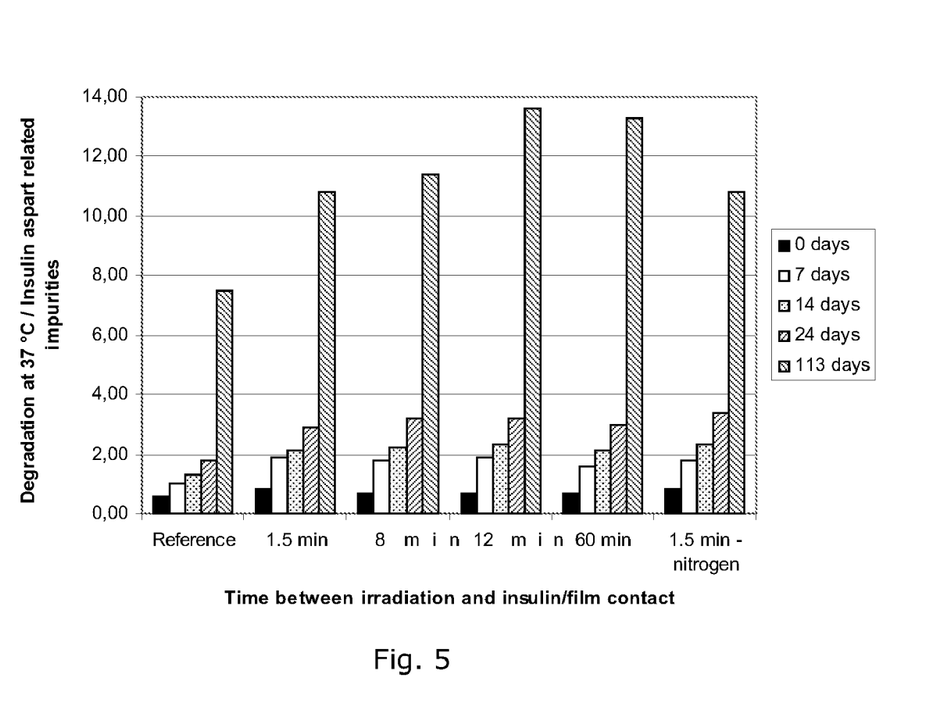
FIGS. 5-9 are graphs and charts illustrating tests performed as described in the Example below.

From FIG. 5 it is observed that the rest time between irradiation and insulin/film contact does seem to have an impact on chemical stability. No difference is observed between samples: 1.5 min and 8 min. Samples: 60 min and 12 min have dissimilar chemical stability compared to the other samples. Assay data from this study indicates that water evaporation from sample 12 min, 60 min and 8 min had taken place. This could compromise the validity of stability data obtained.

In study 2 and 3 the film was converted into reservoirs as quickly as possible after irradiation. For estimating the time effect, time between irradiation and insulin/film contact was varied between 1 h and the lowest practical possible time (½-2 minutes).

Figure 6:
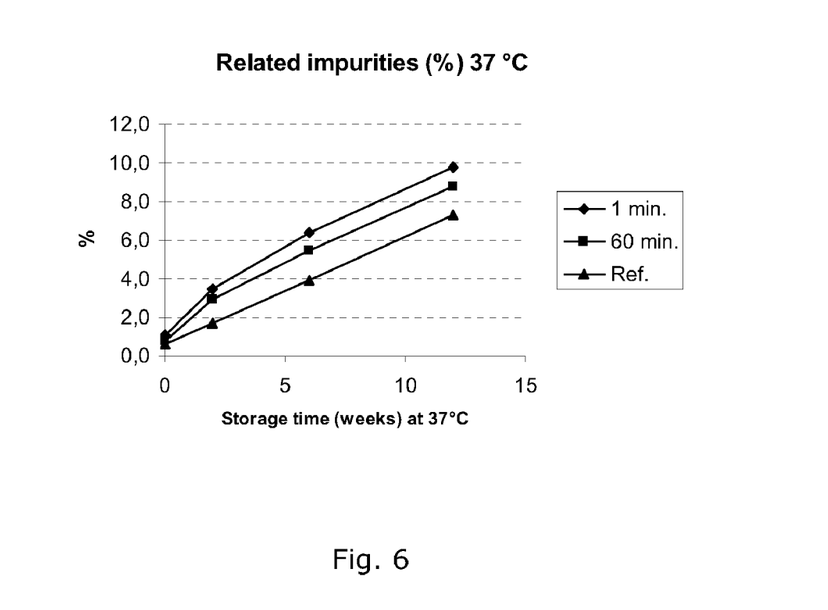
Figure 7:
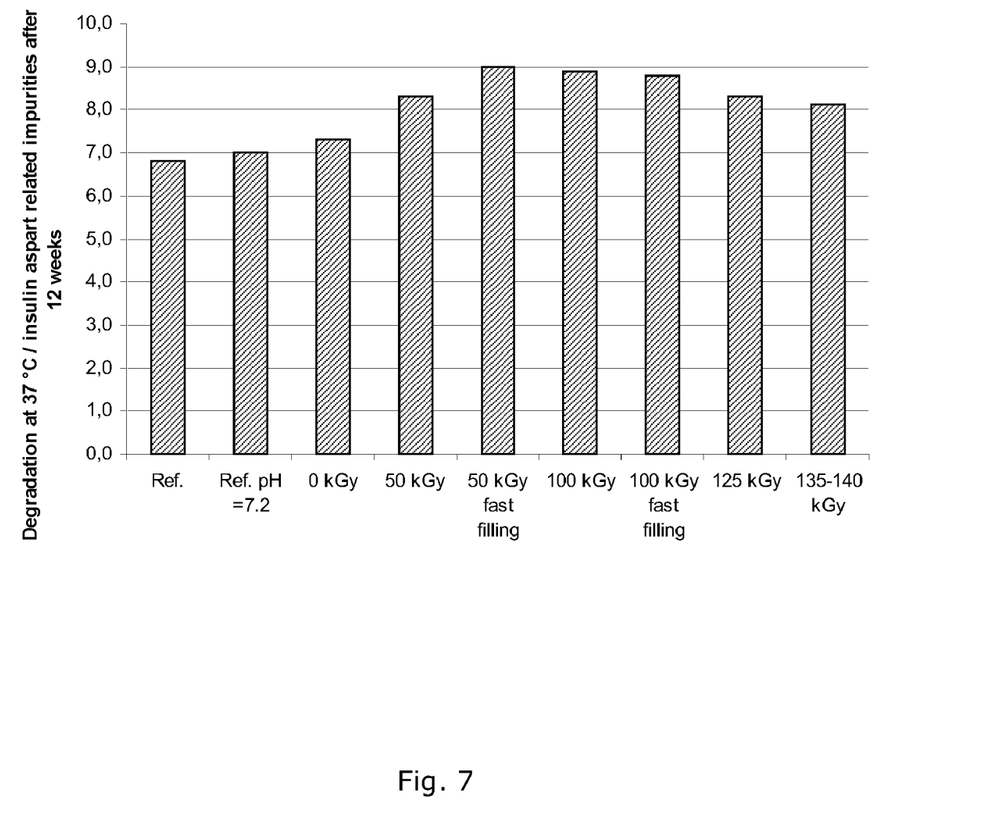

From FIGS. 6 and 7 it is observed that the time between irradiation and filling does have an impact on chemical stability.

In study 3 different doses were applied. It is observed that the chemical stability of insulin aspart is not very sensitive to irradiation dose.

Disregarding data in FIG. 5 it is observed from FIGS. 6 and 7 that the difference between level of related impurities in reservoirs filled just after irradiation and glass reference is From Table 2 it is observed that in samples 11, 12, 13, 14 and 16 the level of related impurities is approximately 2% higher than glass reference. These samples have not received any heat treatment. A difference between sample 14 and (11, 12, 13 and 16) is not observed.

Generally heating of the film improves chemical stability.

In study 5 higher temperatures were applied:

When the temperature is raised to 90° C. in the film heating process, an improved chemical stability is obtained. From FIG. 8 a time dependency is still present, but generally the difference between heat treated films and glass reference is very limited. Antioxidant was added to one film sample, but a positive effect is not observed in chemical stability.

The high evaporation in some samples compromises the stability data in FIG. 5 (Study 1). Furthermore the study was performed as an immersion study. In the performed immersion studies the ratio between liquid and gas phase was about 50%. This means that volatile components from the irradiated film samples may have moved to the gas phase to a much higher degree than in closed film reservoirs.

In study 2 and 3 the stability data is based on reservoirs with a minimum amount of air. The data from FIGS. 6 and 7 indicates that the stability of insulin aspart is dependent on the time between irradiation and insulin filling.

Figure 8:
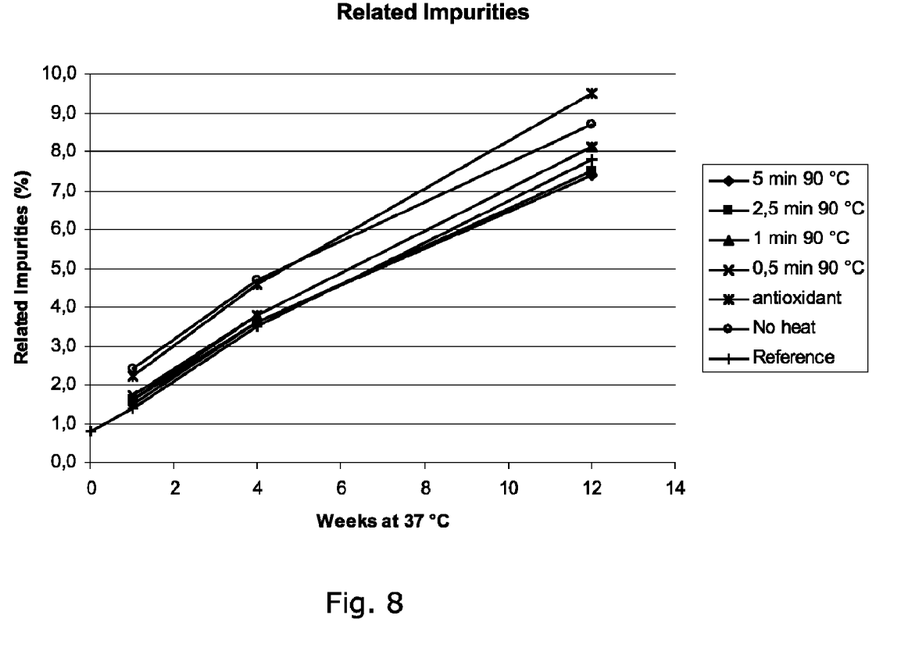

Heating the film after irradiation has a pronounced positive effect on chemical stability (Table 1 and FIG. 8). Heating 2.5-5 min. at 90° C. secures stability similar to glass references (FIG. 8).

In the above mentioned heating processes, the temperatures are measured in the surroundings to the film. The actual film temperature was not measured during the heat treatments, but it can generally be assumed that the film temperature was not the same as the surrounding temperature in the short time treatments (relatively slow convection heat transfer). Table 3 shows comparison of treatments. The difference between glass and reservoir was calculated by subtracting related impurities data between reservoirs at glass at week 12.

TABLE 3

| Study | Treatment | Heat process | Difference between glass and reservoir week 12 |
|---|---|---|---|
| 2 | Fast filling, Dose: 60 kGy | No | 2.5% |
| 3 | Fast filling, Dose: 50 kGy | No | 2.2% |
| 4 | Fast filling, Dose: 60 kGy | No | 2.1% |
| 4 | Fast filling, Dose: 35 kGy | No | 2.4% |
| 5 | Fast filling, Dose: 35 kGy | No | 0.9% |
| 4 | 60 min at room temperature, Dose: 60 kGy | No | 1.9% |
| 3 | 60 min at room temperature, Dose: 50 kGy | No | 1.5% |
| 4 | 5 min at 60 degrees, Dose: 60 kGy | Yes | 1.2% |
| 4 | 5 min at 60, Dose: 35 kGy | Yes | 0.9% |
| 5 | 5 min at 90, Dose: 35 kGy | Yes | −0.4% (**) |
| 5 | 2.5 min at 90, Dose: 35 kGy | Yes | −0.3% (**) |

In the two tests performed in study 5 the reservoirs performed better than corresponding tests in glass material.

From table 3 it is observed that all reservoirs filled just after irradiation generally results in higher level of degradation. The fast filling sample of study 5 performs better than other fast filling samples. This indicates that filling just after irradiation could create not only a higher degradation level, but also a higher variation between samples.

1 hour at room temperature improves the stability, but heating at 60° C. and especially at 90° C. improves the stability to the same level as if stored in glass vials.

The material in the inner and outer layer in the reservoir film is low density polyethylene (LDPE). It is well known that LDPE will soften as the crystalline melting point is approached. The crystalline melting point of LDPE is in the range 110° C.-120° C. and heating the film to 90° C. will for that reason cause the film to soften and loose mechanical strength.

The heat treatment temperature needs be in good balance between insulin stability and mechanical properties of the film, when the final heat process on the production line is chosen.

Figure 9:
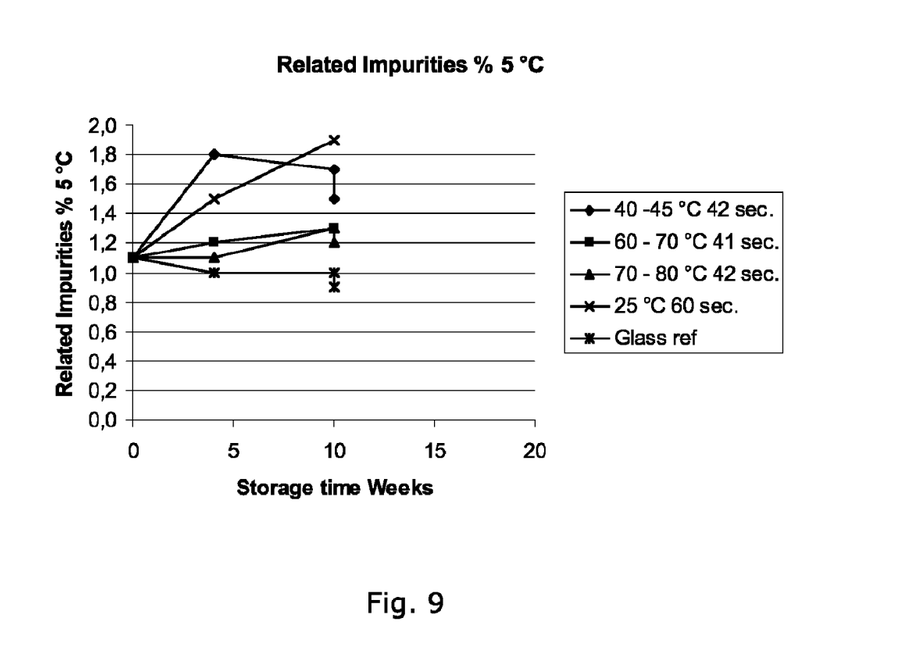

FIG. 9 shows corresponding storage data for storage at 5° C.

The invention claimed is:

1. A method for sterilizing packaging material in packaging for protein containing products, the method comprising:
   irradiating the packaging material using ionizing radiation,
   subsequently accelerating diffusion from the packaging material of protein reactive substances or compounds formed in the packaging material during the irradiation and
   wherein the packaging material is processed such that an impurity level of the protein containing product after storage in the packaging for 10 weeks at 5° C. is within 1.5% of a corresponding impurity level in a comparable protein containing product positioned in a packaging made from a sterilized glass material under similar storage conditions.

2. A method according to claim 1, wherein the irradiating is performed using an electron beam.

3. A method according to claim 1, wherein the accelerating diffusion is performed in such a manner that diffusion of protein reactive substances or compounds formed in a surface region of the packaging material is accelerated.

4. A method according to claim 1, wherein the accelerating diffusion comprises heating the irradiated packaging material.

5. A method according to claim 4, wherein the heating comprises heating the irradiated packaging material to a temperature which does not exceed 200° C.

6. A method according to claim 5, wherein the heating comprises heating the irradiated packaging material to a temperature within the temperature interval 40° C. to 95° C.

7. A method according to claim 4, wherein the heating is performed using infrared radiation.

8. A method according to claim 4, wherein the heating is performed using an oven.

9. A method according to claim 4, wherein the heating is performed by applying a flow of heated air to the packaging material.

10. A method according to claim 1, wherein the accelerating diffusion comprises subjecting the packaging material to a vacuum.

11. A method according to claim 1, wherein the accelerating diffusion is performed substantially immediately after the irradiation.

12. A method according to claim 1, further comprising forming a packaging, wherein at least part of said packaging being made from the packaging material.

13. A method according to claim 12, wherein the packaging material is a foil, and wherein the forming a packaging comprises welding two foil layers together, thereby forming a reservoir.

14. A method according to claim 12, wherein a product is stored in the packaging.

15. A method according to claim 1, wherein the method is an inline process.

16. A method according to claim 1, wherein the packaging material is a polymer material.

17. A method according to claim 1, wherein the method is performed in a sterile environment.

18. A method for sterilizing polymer packaging material in packaging for protein containing products, the method comprising:
   irradiating the polymer packaging material using ionizing radiation,
   subsequently processing the polymer packaging material in such a manner that any protein reactive substances or compounds formed in the polymer packaging material during the irradiation are at least partly removed or rendered unreactive with respect to proteins,
   positioning a protein containing product in packaging formed by the polymer packaging material, and
   sealing the packaging having the protein containing product positioned therein,
   wherein the processing is performed in such a manner that an impurity level in the protein containing product after storage in the packaging for 10 weeks at 5° C. is within 1.5% of a corresponding impurity level in a comparable protein containing product positioned in a packaging made from a sterilized glass material under similar storage conditions.

19. A method according to claim 18, wherein the processing is performed by accelerating diffusion from the packaging material of protein reactive substances or compounds formed in the packaging material during the irradiation step.

20. A method according to claim 18, wherein the processing comprises heating the packaging material.

21. A method according to claim 20, wherein the heating comprises heating the packaging material to a temperature which does not exceed 200° C.

22. A method according to claim 21, wherein the heating comprises heating the packaging material to a temperature within the temperature interval 40° C. to 95° C.

23. A method according to claim 20, wherein the heating is performed by applying a flow of heated air to the packaging material.

24. A method according to claim 18, wherein the processing comprises subjecting the packaging material to a vacuum.

* * * * *